United States Patent [19]

Iversen

[11] Patent Number: 5,935,164
[45] Date of Patent: Aug. 10, 1999

[54] LAMINATED PROSTHESIS AND METHOD OF MANUFACTURE

[75] Inventor: Alfred A. Iversen, Wayzata, Minn.

[73] Assignee: PMT Corporaton, Chanhassen, Minn.

[21] Appl. No.: 08/805,687

[22] Filed: Feb. 25, 1997

[51] Int. Cl.⁶ .............................. A61F 2/12; A61F 2/04; A61F 25/10

[52] U.S. Cl. .............................. 623/8; 264/294; 264/305; 264/308; 264/310; 427/2.28; 427/2.3; 623/12; 604/96

[58] Field of Search ........................... 427/2.3, 346, 331, 427/413, 430.1, 434.5, 2.28; 623/8, 12; 604/264, 96; 264/308, 310, 305, 294

[56] References Cited

U.S. PATENT DOCUMENTS

| 3,030,251 | 4/1962 | La Bore et al. ................ 427/413 |
| 3,293,663 | 12/1966 | Cronin . |
| 3,366,975 | 2/1968 | Pangman . |
| 3,559,214 | 2/1971 | Pangman . |
| 3,654,017 | 4/1972 | Ropiequet et al. ................ 156/251 |
| 3,740,262 | 6/1973 | Agostinelli ................ 427/2.3 |
| 3,852,832 | 12/1974 | McGhan et al. ................ 3/36 |
| 3,936,517 | 2/1976 | Thomas ................ 264/28 |
| 4,137,354 | 1/1979 | Mayes, Jr et al. ................ 156/175 |
| 4,143,109 | 3/1979 | Stockum ................ 264/112 |
| 4,178,643 | 12/1979 | Cox, Jr. ................ 3/36 |
| 4,190,040 | 2/1980 | Schulte ................ 128/1 R |
| 4,217,889 | 8/1980 | Radovan et al. ................ 128/1 R |
| 4,298,997 | 11/1981 | Rybka ................ 3/36 |
| 4,455,691 | 6/1984 | Redinger et al. ................ 3/36 |
| 4,472,226 | 9/1984 | Redinger et al. ................ 156/246 |
| 4,475,976 | 10/1984 | Mittelstadt et al. ................ 156/286 |
| 4,481,335 | 11/1984 | Stark, Jr. ................ 525/261 |

(List continued on next page.)

FOREIGN PATENT DOCUMENTS

| 196 821 | 10/1986 | European Pat. Off. . |
| 0293256 | 5/1988 | European Pat. Off. . |
| 0422302 | 10/1989 | European Pat. Off. . |
| 0412703 | 7/1990 | European Pat. Off. . |
| 0416846 | 9/1990 | European Pat. Off. . |

OTHER PUBLICATIONS

S. R. Taylor and D. F. Gibbons, "*Effect of Surface Texture on the Soft Tissue Response to Polymer Implants*", Journal of Biomedical Materials Research, vol. 17, 1983, pp. 205–227. (no month).

Professor K. Gerhard Brand's letter to Dr. R. K. Donis. (Feb. 1985).

George J. Picha and Dennis J. Siedlak, "*Ion–Beam Microtexturing of Biomedicals*", MDGDI, Apr., 1984, pp. 39–42.

"*Proven Generation*", The Becker Expander/Mammary Prosthesis, Nov., 1987.

Steven Herman, M.D., "*The Meme Implant*", Plastic and Reconstructive Surgery, Mar., 1984, pp. 411–414.

(List continued on next page.)

*Primary Examiner*—Diana Dudash
*Attorney, Agent, or Firm*—Anthony G. Eggink; Jeffrey L. Cameron

[57] ABSTRACT

A method of manufacturing a laminated item such as a prosthesis or tissue expander having a flexible, expandable membrane surrounding an interior lumen to enhance the strength and performance of the membrane comprises the steps of applying a first layer of a fluid, resilient, stretchable material to a mandrel; allowing the fluid material to drain off the mandrel in a first flow direction; allowing the fluid material to harden to form a resilient, stretchable first layer on the mandrel; applying a second layer of the fluid material on the first layer; changing the orientation of the mandrel to allow the fluid material to drain off the mandrel in a second flow direction, the second flow direction being at an angle to the first flow direction; and allowing the fluid material to harden to form a resilient, stretchable second layer on the first layer.

30 Claims, 2 Drawing Sheets

U.S. PATENT DOCUMENTS

| | | | |
|---|---|---|---|
| 4,531,244 | 7/1985 | Hamas | 623/8 |
| 4,543,088 | 9/1985 | Bootman et al. | 604/93 |
| 4,643,733 | 2/1987 | Becker | 623/8 |
| 4,648,880 | 3/1987 | Brauman | 623/8 |
| 4,662,883 | 5/1987 | Bell et al. | 623/8 |
| 4,666,447 | 5/1987 | Smith et al. | 623/8 |
| 4,671,255 | 6/1987 | Dubrul et al. | 128/1 R |
| 4,735,982 | 4/1988 | Orndorff, Jr. | 524/269 |
| 4,738,657 | 4/1988 | Hancock et al. | 604/93 |
| 4,772,284 | 9/1988 | Jefferies et al. | 623/8 |
| 4,775,379 | 10/1988 | Fogarty et al. | 623/8 |
| 4,798,584 | 1/1989 | Hancock et al. | 604/93 |
| 4,840,615 | 6/1989 | Hancock et al. | 604/93 |
| 4,841,948 | 6/1989 | Bauer et al. | 128/897 |
| 4,841,992 | 6/1989 | Sasaki et al. | 128/899 |
| 4,859,712 | 8/1989 | Cox | 521/62 |
| 4,889,744 | 12/1989 | Quaid | 427/2 |
| 4,890,866 | 1/1990 | Arp | 285/243 |
| 4,906,423 | 3/1990 | Frisch | 264/48 |
| 4,930,535 | 6/1990 | Rinehold | 137/15 |
| 4,933,040 | 6/1990 | Wesley, Jr. | 156/245 |
| 4,944,749 | 7/1990 | Becker | 623/8 |
| 4,955,909 | 9/1990 | Ersek et al. | 623/11 |
| 4,960,425 | 10/1990 | Yan et al. | 623/8 |
| 4,992,312 | 2/1991 | Frisch | 427/333 |
| 5,002,572 | 3/1991 | Picha | 623/11 |
| 5,005,591 | 4/1991 | Austad | 128/899 |
| 5,007,929 | 4/1991 | Quaid | 623/8 |
| 5,019,101 | 5/1991 | Purkait et al. | 623/8 |
| 5,022,942 | 6/1991 | Yan et al. | 156/219 |
| 5,083,576 | 1/1992 | Ruiz-Razura et al. | 128/898 |
| 5,092,348 | 3/1992 | Dubrul et al. | 128/899 |
| 5,116,370 | 5/1992 | Foglietti | 623/8 |
| 5,138,719 | 8/1992 | Orlianges et al. | 2/168 |
| 5,188,872 | 2/1993 | Quigley | 428/36.2 |
| 5,196,263 | 3/1993 | Melby et al. | 428/327 |
| 5,201,715 | 4/1993 | Masters | 604/175 |
| 5,236,454 | 8/1993 | Miller | 623/8 |
| 5,344,451 | 9/1994 | Dayton | 623/7 |
| 5,354,338 | 10/1994 | Ledergerber | 623/8 |
| 5,407,612 | 4/1995 | Gould et al. | 264/24 |
| 5,480,430 | 1/1996 | Carlisle et al. | 623/8 |
| 5,496,370 | 3/1996 | Hamas | 623/11 |
| 5,599,576 | 2/1997 | Opolski | 427/2.3 |
| 5,612,083 | 3/1997 | Huang et al. | 427/413 |

OTHER PUBLICATIONS

Thomas D. Rees, M.D., et al., "*The Use of Inflatable Breast Implants*", Plastic and Reconstructive Surgery, Dec., 1973, pp. 609–615. (no month).

Surgitek Gel/Saline Mammary Implant, Jan., 1984.

Hilton Becker, M.D., "*Breast Reconstruction Using an Inflatable Breast Implant with Detachable Reservoir*", Plastic and Reconstructive Surgery, Apr., 1984, pp. 678–683.

James C. Sipio, M.D., et al., "*Soft Tissue Expansion of the Ureter and Bladder in the Dog*", Sep., 1986.

Francis A. Marzoni, M.D., et al, "*An Experimental Study of Silicone as a Soft Tissue Substitute*", Plastic and Reconstructive Surgery, Dec., 1959.

Julio C. Davila, et al, "*Some Physical Factors Affecting the Acceptance of Synthetic Materials as Tissue Implants*", 1968. (no month).

Benjamin F. Edwards, M.D., "*Teflon–Silcone Breast Implants*", Plastic and Reconstructive Surgery, Nov., 1963, pp. 519–526. (no month).

Robert L. Whalen, "*Improved Textured Surfaces for Implantable Prosthesis*", Trans Am Soc Artif Intern Organs, 1988, vol. XXXIV, pp. 887–892. (no month).

McGhan Biocell Textured Mammary Implant, Oct., 1987.

V. R. Pennisi, M.D., "*Polyurethane–Covered Silicone Gel Mammary Prosthesis for Successful Breast Reconstruction*", Aesthetic Plastic Surgery, 1985. (no month).

Franklin L. Ashley, M.D., "*A New Type of Breast Prosthesis*", Plastic and Reconstructive Surgery, May, 1970, pp. 421–424. (no month).

D. W. Brown, et al, "*The Kinetics of Hydrolytic Aging of Polyester Urethane Elastomers*", Jul., 1979.

Roger T. Sherman, M.D., et al, "*The Biological Fate of Implanted Rigid Polyurethane Foam*", Journal of Surgical Research, Mar., 1969, pp. 167–171.

LAMINATED PROSTHESIS AND METHOD OF MANUFACTURE

BACKGROUND OF THE INVENTION

In the field of plastic surgery, it has become a frequent practice to implant a prosthesis in the area of the female breast for reconstruction or augmentation. In the case of reconstruction, cancerous, pre-cancerous or other abnormal or damaged tissue has been removed. This creates a void where the tissue has been removed. A prosthesis may then be inserted through an incision to fill this void. The prosthesis then becomes a permanent replacement for the damaged tissue which has been removed, and its purpose is to restore the body contour to its original configuration. The prosthesis then furnishes support for the surrounding body tissue and organs to preserve as closely as possible the original appearance of the body.

Skin and its subcutaneous tissue can be greatly expanded in area if the expansion is accomplished gradually. The extension of the skin over the pregnant female's abdomen is one example. A tissue expander is a device designed to be implanted beneath the skin then inflated to stretch the overlying skin and subcutaneous tissues. One use of such tissue expanders is to generate an increased surface area of skin to be used for grafting or reconstruction. Another use is to slowly expand the overlying skin to create a pocket beneath the skin and subcutaneous tissue to receive a permanent prosthesis such as a mammary implant.

Both mammary prostheses and tissue expanders have the common property that they have an outer resilient, stretchable membrane which encloses a space filled with a fluid or gel. The outer membrane must be stretchable to accommodate filling the implant with increasing amounts of fluid. At the same time, the outer membrane must be tough and resistant to tearing as the implant is expanded.

Other implantable medical devices such as transcutaneous catheters, artificial hearts, left ventricle assist devices have some of the common properties of mammary prostheses and tissue expanders discussed above.

Medical implants such as the above have generally been manufactured by applying a fluid layer of a resilient, stretchable material such as silicone rubber to a mandrel or mold, then allowing the silicone rubber to cure or harden on the mandrel. The implant is then removed from the mandrel. However, none of the earlier methods of manufacture take advantage of the structural engineering principle of multiple, multi-directional layers.

It is the intent of the present invention to provide a novel manufacturing method for a layered implant and a layered implant with the layers crossing each other at an angle, thereby providing increased strength and performance.

SUMMARY OF THE INVENTION

A method of manufacturing a laminated item such as a prosthesis or tissue expander having a flexible, expandable membrane surrounding an interior lumen to enhance the strength and performance of the membrane comprises the steps of applying a first layer of a fluid, resilient, stretchable material to a mandrel; allowing the fluid material to drain off the mandrel in a first flow direction; allowing the fluid material to harden to form a resilient, stretchable first layer on the mandrel; applying a second layer of the fluid material on the first layer; changing the orientation of the mandrel to allow the fluid material to drain off the mandrel in a second flow direction, the second flow direction being at an angle to the first flow direction; and allowing the fluid material to harden to form a resilient, stretchable second layer on the first layer.

A principle object and advantage of the present invention is that it applies the structural engineering principle of multiple, multi-directional layers in the membrane to enhance the strength and performance of the item.

Another principle object and advantage of the present invention is that the multiple, multi-directional layers may be applied to form the item merely by changing the orientation of the mandrel so that each layer of material drains off the mandrel in a different direction. This makes manufacture of the multiple, multi-directional layers quite simple.

Another principle object and advantage of the present invention is that the fluid material which forms the multiple, multi-directional layers may include filaments of a stretchable material to provide added strength to the multiple, multi-directional layers.

DETAILED DESCRIPTION OF THE PREFERRED EMBODIMENTS

Figure 1:
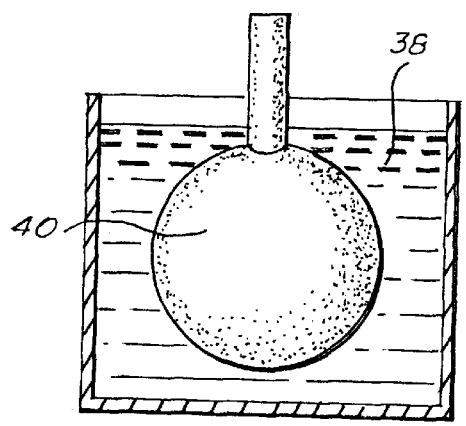
FIG. 1 shows a mandrel being dipped into a fluid material which will harden to form a resilient, stretchable layer.

The laminated item of the present invention is generally shown in the Figures as reference numeral 20.

The laminated item 20 consists of a flexible, expandable membrane 22 surrounding a lumen 24 which may contain a fluid or gel.

The membrane 22 comprises a plurality of layers 26, 28, 30 (three layers are shown in the Figures but this should not be viewed as limiting).

Figure 10:
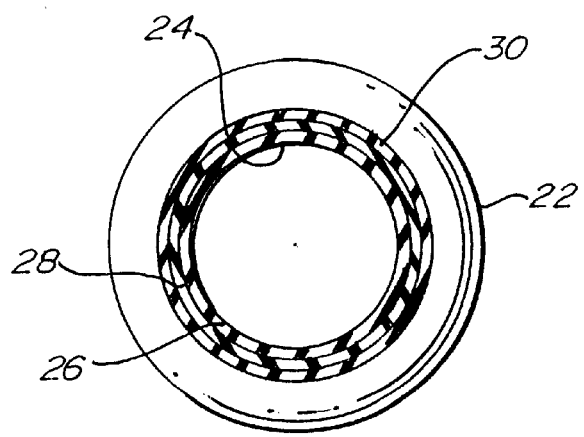
FIG. 10 is a cross section along the section lines 10—10 in FIG. 9.

Each of the layers 26, 28, 30 is oriented at an angle to the layer on either side. For example, the "grain" or direction of primary stretchability of layer 26 may be visualized as coming out of the page in FIG. 10. The "grain" or direction of primary stretchability of layer 28 may then be parallel to the page. The "grain" or direction of primary stretchability of layer 30 may then again be visualized as coming out of the page. All the layers may be at any angle to each other, in the preferred embodiment each layer 26, 28, 30 is oriented at an angle of 90 degrees to the layer on either side.

Preferably, the laminated item 20 is composed of silicone rubber. The laminated item 20 may be, for example, a mammary prosthesis or a tissue expander, but may also be any other item which may benefit from the strength enhancement caused by the multiple, multi-directional layers.

Figure 8:
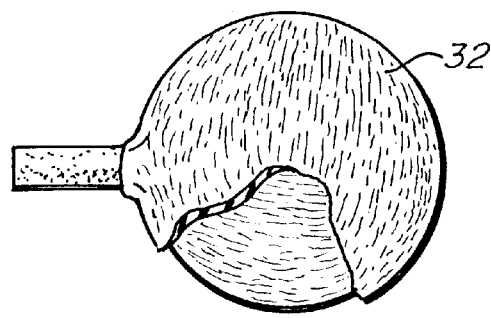
FIG. 8 shows a second embodiment of FIG. 5 in which the fluid material contains filaments of stretchable material and these filaments have been oriented in two flow directions.
Figure 9:
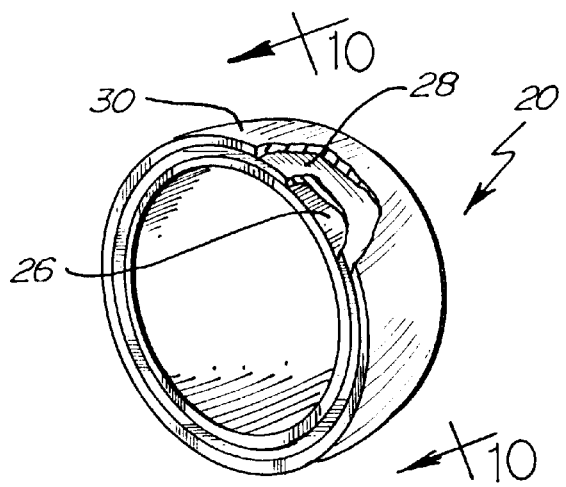
FIG. 9 shows the completed article with structure cut away to show the first, second, and third layers.

To enhance the strength of the multiple layers, filaments 32 of a stretchable material such as silicone rubber may be embedded in each layer, as shown in FIG. 8.

The laminated item may be manufactured according to a process as described below.

In the first step, a fluid material 38 is applied to a mandrel 40 which has the overall shape of the item to be created. The fluid material may be any substance which hardens to form a resilient, stretchable layer. Preferably, the fluid material 38 is silicone rubber. FIG. 1 shows the fluid material 38 being applied to the mandrel 40 by dipping the mandrel 40 into the fluid material 38. Alternatively, the fluid material 38 may be sprayed, painted, or brushed onto the mandrel 40.

Figure 2:
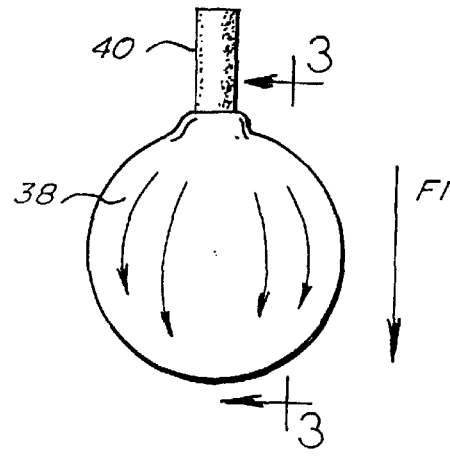
FIG. 2 shows the mandrel oriented to allow the fluid material to drain off the mandrel in a first flow direction.

Next, the fluid material 38 is allowed to drain off the mandrel 40 in a first flow direction F1 as shown by the arrows in FIG. 2. It will be apparent to one of ordinary skill in the art that this may be done simply by suspending the mandrel 40 and allowing the fluid material 38 to drain off under the influence of gravity. However, any other way of producing a flow of the fluid material in one direction along the surface of the mandrel may also be employed. For example, the mandrel could be dragged through the fluid material or suction could be used to produce a flow in the indicated direction.

Figure 3:
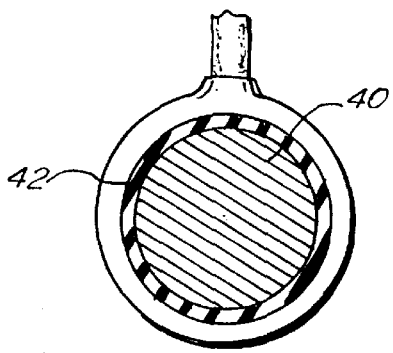
FIG. 3 is a cross-section along the lines 3 3 of FIG. 2 after the fluid material has been allowed to harden to form a resilient, stretchable first layer on the mandrel.

Next, the fluid material 38 is allowed to harden to form a resilient, stretchable first layer 42 on the mandrel 40 (see FIG. 3). Any method of hardening appropriate to the fluid material may be used. For example, the fluid material 38 may be allowed to air dry. Alternatively, the fluid material 38 may be vulcanized.

As a result, the "grain" or direction of primary stretchability of the first layer 42 will lie along the direction of the first flow direction.

Next, a second layer of the fluid material 38 is applied to the mandrel by any of the methods discussed above, i.e., dipping, spraying, painting or brushing. The method used for applying the second layer may or may not be the same as the method used for applying the first layer.

Figure 4:
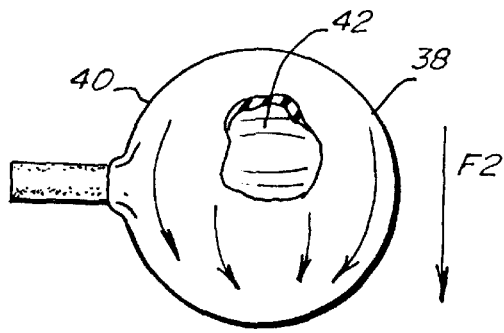
FIG. 4 shows the mandrel, after a second layer of fluid material has been applied, being oriented to allow the fluid material to drain off the mandrel in a second flow direction at an angle to the first flow direction.

The orientation of the mandrel 40 is then changed to allow the fluid material 38 to drain off the mandrel 40 in a second flow direction F2 as shown in FIG. 4. The second flow direction is at an angle to the first flow direction F1. It will be apparent to one of ordinary skill in the art that this can be accomplished by suspending the mandrel at a different angle to the vertical from that used in producing the first flow direction F1. Alternatively, the mandrel 40 may be dragged through the fluid material in a direction opposite to F2 to produce the desired flow, or suction may be used to produce the desired flow. Preferably, the second flow direction F2 is at angle of 90 degrees to the first flow direction F1.

Figure 5:
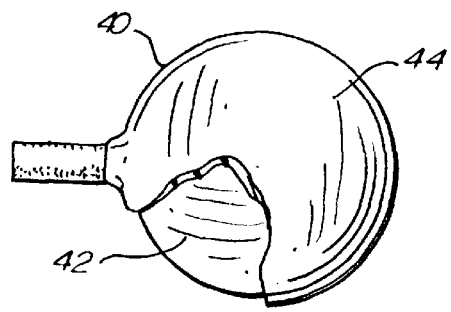
FIG. 5 shows the mandrel with first and second layers after the second layer has hardened.
Figure 6:
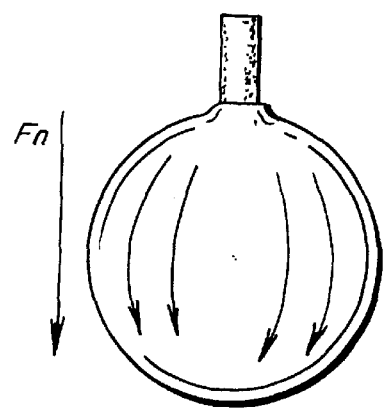
FIG. 6 shows the mandrel, after a third layer of fluid material has been applied, being oriented to allow the fluid material to drain off the mandrel in a third flow direction at an angle to the second flow direction.
Figure 7:
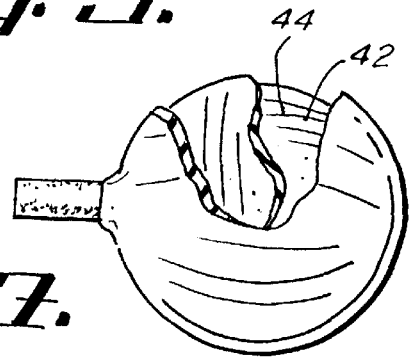
FIG. 7 shows the mandrel with first, second, and third layers after the third layer has hardened.

Next, the fluid material 38 is hardened to form a resilient, stretchable second layer 44 on the first layer 42, as shown in FIG. 5.

It will be seen that the first layer 42 and the second layer 44, lying at an angle to each other, enhance the strength and performance of the item 20, in a manner similar to that in which the layers in plywood form a strong article. Any force tending to tear the first layer 42 along the direction F1 will be countered by the resistance of the second layer 44, and vice-versa. If the item 20 is a mammary implant, the natural tendency of the fluid within the lumen 24 to bulge the membrane 22 will also be countered by the overlapping, opposing first layer 42 and second layer 44.

The strength of the first layer 42 and second layer 44 may be increased by suspending filaments 32 of stretchable material in the fluid material 28. As the fluid material 28 drains off the mandrel 40, the filaments 32 will tend to line up with either the flow direction F1 or the flow direction F2, thus enhancing the strength of the first layer 42 and second layer 44 accordingly. See FIG. 8. The filaments may be, for example, silicone rubber or latex. However, any filament may be used that is stretchable.

Optionally, additional layers of fluid material 28 may be applied to the second layer 44 in similar fashion to the steps described above. That is, each additional layer is applied on the previous hardened layer by dipping, spraying, painting or brushing; the orientation of the mandrel is changed to allow the fluid material 28 to drain off the mandrel 40 in an additional flow direction $F_n$, each new flow direction $F_n$ being at angle to the previous flow direction $F_{n-1}$; and the fluid material 28 is allowed to hardened as described above.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A method of manufacturing a self-supporting, tissue expanding item constructed of multiple layers forming a molded flexible, expandable membrane surrounding and defining an interior lumen, said method comprising the steps of:
    (a) applying a fluid material comprised of a polymer to a mandrel, said fluid material having filaments of a stretchable material mixed therein;
    (b) draining said fluid material off the mandrel in a first flow direction whereby said polymer and said filaments are generally oriented in said first flow direction;
    (c) allowing said fluid material to harden to form a resilient, stretchable first layer on the mandrel;
    (d) applying a second layer of the same said fluid and filament material onto said first layer;
    (e) changing the orientation of the mandrel to allow the fluid material to drain off the mandrel in a second flow direction whereby said polymer and said filaments comprising said second layer are generally oriented in said second flow direction, the second flow direction being at a first angle with respect to said first flow direction;
    (f) allowing the fluid material to harden to form a resilient, stretchable second layer on said first layer; and
    (g) removing said molded multi-layered item from said mandrel whereby the cooperation of the different directional layers form a strengthened, self-supporting, multi-layered, molded item.

2. The method of claim 1, wherein the fluid material is silicone rubber.

3. The method of claim 1, wherein the second flow direction is at an angle of 90 degrees to the first flow direction.

4. The method of claim 1, wherein the first layer and second layer are applied to the mandrel by dipping the mandrel into the fluid material.

5. The method of claim 1, wherein the first layer and second layer are applied to the mandrel by spraying the first layer and second layer onto the mandrel.

6. The method of claim 1, wherein the first layer and second layer are applied to the mandrel by brushing the first layer and second layer onto the mandrel.

7. The method of claim 1, wherein the first layer and second layer are applied to the mandrel by painting the first layer and second layer onto the mandrel.

8. The method of claim 1, comprising the steps of applying additional layers of fluid material to the second layer, changing the orientation of the mandrel to allow the fluid material to drain off the mandrel in additional flow directions, each flow direction being at an angle to the preceding flow direction, and allowing the fluid material to harden to form additional resilient, stretchable layers.

9. The method of claim 8, wherein each additional flow direction is at a 90 degree angle to the previous flow direction.

10. The method of claim 1, wherein the fluid material contains filaments of a stretchable material to provide added strength to the first layer and second layer.

11. The method of claim 10 wherein the filaments are selected from the group consisting of silicone rubber and latex.

12. A method of manufacturing a self-supporting, tissue expanding item constructed of multiple layers forming a molded flexible, expandable membrane surrounding and defining an interior lumen, said method comprising the steps of:

(a) applying a fluid material comprised of an orientable polymer to a mandrel;

(b) draining said fluid material off the mandrel in a first flow direction;

(c) allowing said fluid material to harden to form a resilient, stretchable first layer on the mandrel;

(d) applying a second layer of the same said fluid material on said first layer;

(e) changing the orientation of the mandrel to allow the fluid material to drain off the mandrel in a second flow direction, the second flow direction being at a first angle with respect to said first flow direction;

(f) allowing the fluid material to harden to form a resilient, stretchable second layer on said first layer;

(g) applying additional layers of fluid material to said second layer, changing the orientation of the mandrel to allow the fluid material to drain off the mandrel in additional flow directions, each flow direction being at a second angle with respect to the preceding flow direction, and allowing the fluid material to harden to form additional resilient, stretchable layers; and (h) removing said multi-layered item from said mandrel whereby the cooperation of the different directional layers forms a strengthened, multi-layered, molded item.

13. The method of claim 12, wherein the fluid material is silicone rubber.

14. The method of claim 12, wherein the second flow direction is at an angle of approximately 90 degrees to the first flow direction.

15. The method of claim 12, wherein the first layer, second layer, and additional layers are applied to the mandrel by dipping the mandrel into the fluid material.

16. The method of claim 12, wherein the first layer, second layer, and additional layers are applied to the mandrel by spraying the fluid material onto the mandrel.

17. The method of claim 12, wherein the first layer, second layer, and additional layers are applied to the mandrel by brushing the fluid material onto the mandrel.

18. The method of claim 12, wherein the first layer and second layer are applied to the mandrel by painting the fluid material onto the mandrel.

19. The method of claim 12, wherein each additional flow direction is at approximately a 90 degree angle to the previous flow direction.

20. The method of claim 12, wherein the fluid material contains filaments of a stretchable material to provide added strength to the first layer, second layer, and additional layers.

21. The method of claim 20, wherein the filaments are selected from the group consisting of silicone rubber and latex.

22. A method of manufacturing a self-supporting, tissue expanding item constructed of multiple, layers forming a flexible, expandable and self-supporting, molded membrane surrounding and defining an interior lumen, said method comprising the steps of:

(a) applying a fluid material comprised of an orientable polymer to a mandrel, said fluid material further containing filaments of a stretchable material and being mixed in said fluid material;

(b) draining said fluid material off the mandrel in a first flow direction whereby said polymer and said filaments are generally oriented in said first flow direction;

(c) allowing the fluid material to harden to form a resilient, stretchable first layer on the mandrel;

(d) applying a second layer of the same said fluid material on the first layer;

(e) changing the orientation of the mandrel to allow the fluid material to drain off the mandrel in a second flow direction whereby said polymer and said filaments comprising said second layer are generally oriented in said second flow direction, the second flow direction being at a first angle with respect to said first flow direction;

(f) allowing the fluid material to harden to form a resilient, stretchable second layer on the hardened first layer;

(g) applying additional layers of said fluid material to the second hardened layer, changing the orientation of the mandrel to allow the fluid material to drain off the mandrel in additional flow directions, each flow direction being at an angle with respect to the preceding flow direction, and allowing the fluid material to harden to form additional resilient, stretchable layers; and (h) removing said multi-layered item from said mandrel whereby the cooperation of the different directional layers forms a strengthened, multi-layered, molded item.

23. The method of claim 22, wherein the filaments are selected from the group consisting of silicone rubber and latex.

24. A multi-layered, self-supporting, molded item comprising a flexible, expandable membrane having a plurality of consecutive layers of flexible, stretchable material, each said layer of material further containing filaments embedded within said layer, each of said layers being oriented at a first angle with respect to the layer adjacent to it, said membrane surrounding and defining a lumen constructed and arranged to be filled with fluid or gel, whereby the cooperation of the different directional layers forms a molded, self-supporting, multi-layered item.

25. The multi-layered item of claim 24, wherein the flexible material is silicone rubber.

26. The multi-layered item of claim 24, wherein the item is a mammary prosthesis.

27. The multi-layered item of claim 24, wherein the item is a tissue expander.

28. The multi-layered item of claim 24, wherein each layer is oriented at an angle of approximately 90 degrees to the layer on either side.

29. The multi-layered item of claim 24, further comprising filaments of stretchable material embedded in each layer.

30. The multi-layered item of claim 29, wherein the filaments are selected from the group consisting of silicone rubber and latex.

* * * * *